United States Patent [19]

Koontz

[11] Patent Number: 5,332,551
[45] Date of Patent: Jul. 26, 1994

[54] ATOMIC OXYGEN REACTOR HAVING AT LEAST ONE SIDEARM CONDUIT

[75] Inventor: Steven L. Koontz, League City, Tex.

[73] Assignee: The United States of America as represented by the Administrator of the National Aeronautics and Space Administration, Washington, D.C.

[21] Appl. No.: 997,265

[22] Filed: Feb. 23, 1993

Related U.S. Application Data

[62] Division of Ser. No. 894,505, Jun. 2, 1992, Pat. No. 5,215,790, which is a division of Ser. No. 429,739, Oct. 31, 1989, Pat. No. 5,141,806.

[51] Int. Cl.$^5$ .......................... B01J 15/00; B01J 19/08
[52] U.S. Cl. ........................... 422/129; 156/345; 156/643; 422/186.04; 422/186.05
[58] Field of Search ............... 422/129, 186, 186.04, 422/186.05, 186.06; 156/345, 643

[56] References Cited

U.S. PATENT DOCUMENTS

| | | | |
|---|---|---|---|
| 3,619,403 | 11/1970 | Gorin | 204/312 |
| 4,065,369 | 12/1977 | Ogawa et al. | 422/186.05 X |
| 4,160,690 | 7/1979 | Shibagaki et al. | 422/186.05 X |

OTHER PUBLICATIONS

Koontz et al. "Material Selection for Long Life in LEO: A Critical Evaluation of Atomic Oxygen Testing with Thermal Atom Systems" Proceedings of the 15th Space Simulation Conf. Oct. 31–Nov. 3, 1988 Williamsburg, Va.

Smith, *Journal of Chem. Physics,* vol. 11, pp. 110–125 (1943).

*Primary Examiner*—Robert J. Warden
*Assistant Examiner*—Krisanne M. Thornton
*Attorney, Agent, or Firm*—James M. Cate; Guy M. Miller; Edward K. Fein

[57] ABSTRACT

An apparatus (200) for treating a microporous structure (239) with atomic oxygen. The apparatus (200) includes a main gas chamber (202) for flowing gas in an axial direction and a source (218, 220) of gas, containing atomic oxygen, connected for introducing the gas into the main gas chamber (202). The apparatus (200) employs at least one side arm (228) extending from the main atomic oxygen-containing chamber (202). The side arm (228) has characteristic relaxation times such that a uniform atomic oxygen dose rate is delivered to a specimen (239) positioned transversely in the side arm (228) spaced from the main gas chamber (202).

5 Claims, 2 Drawing Sheets

ATOMIC OXYGEN REACTOR HAVING AT LEAST ONE SIDEARM CONDUIT

This is a division of application Ser. No. 07/894,505 filed Jun. 2, 1992, now U.S. Pat. No. 5,215,790, which is a division of application Ser. No. 07/429,739 filed Oct. 31, 1989, now U.S. Pat. No. 5,141,806.

ORIGIN OF THE INVENTION

The invention described herein was made by employee(s) of the United States Government and may be manufactured and used by or for the Government of the United States of America for governmental purposes without the payment of any royalties thereon or therefor.

1. Technical Field of the Invention

This invention relates to microporous structures with layered interstitial surface treatments, and particularly to microporous silica with such layered surface treatments having utility in chromatographic separation techniques. The invention also relates to methods of preparing such microporous structures employing atomic oxygen, and the design of atomic oxygen reactors. The invention further relates to the activation of aerogel catalysts with atomic oxygen.

2. Background Art

Chromatography involves the flow of a mobile phase over a stationary phase. Liquid chromatography is used for soluble substances, and gas chromatography for volatile substances. As the mobile phase moves past the stationary phase, repeated adsorption and desorption of the solute occurs at a rate determined chiefly by its distribution ratio between the two phases. If the ratio is large enough, the components of the mixture will move at different rates, producing a series of bands or chromatographs by which their identity can be determined. The analysis of many biological samples is commonly performed using a chromatographic technique known as high performance liquid chromatography (HPLC). Typical packing materials employed in HPLC and other chromatographic columns of various lengths include silica gel, alumina, glass beads, polystyrene gel and ion exchange resins. Separation of materials in a sample is effected by the affinity of a sample component or isolate towards the packing material. For example, hydrophobic substances can generally be separated by using hydrophobic octadecylsilane columns or another alkyl-bonded silica column. However, one problem, encountered in the analysis of biological samples with such packing material, is that proteins in many biological samples denature on the hydrophobic surfaces of packing material, adsorb onto the support particulates and accumulate inside the chromatographic column to eventually damage the column. One approach to overcome this problem has been to pretreat the biological sample, such as, for example, by protein precipitation followed by organic extraction, or the removal of proteins and analities on large particulate silica bonded materials, either off-line or as a precolumn. Various solid-phase extraction techniques for sample preparation are reviewed in Tippins, *American Laboratory*, p. 107 (February 1987). These techniques are undesirable, however, because of the additional sample processing and time required.

An alternative approach for avoiding protein denaturation in HPLC analysis of biological samples has been the use of silica packing materials wherein the hydrophobic partitioning phase is confined exclusively to the internal particulate region of a porous silica support, while keeping the external surface of the support hydrophilic and non-adsorptive to proteins. Such chromatographic support material is also known as an internal surface reversed-phase (ISRP) support. It has been known to prepare such ISRP packings using an elaborate procedure. In the conventional ISRP preparation procedure, small-pore-diameter silica is first modified with a glycerylpropyl bonded phase. Polypeptides with hydrophobic moieties which are susceptible to enzyme cleavage are then covalently bound to the glycerylpropyl phase. The derivitized packing is then treated with enzymes to remove the hydrophobic species from only the external surface by selecting enzymes which are too large to enter the internal surface region. Such ISRP supports are described, for example, in Hagestam et al, *Analytical Chemistry*, vol. 57, pp. 1757–1763 (1985); Pinkerton et al, *BioChromatography*, vol. 1, pp. 96–105 (1986); and Pinkerton, *American Laboratory*, pp. 70–76 (April 1988). Pinkerton ISRP columns are commercially available from Regis Chemical Co. ISRP supports having a phase bonded with propylamine-coupled lecithin-imidazolide are described in Pidgeon, *Chemical & Engineering News*, pp. 23–24 (Dec. 12, 1988).

The use of particulate materials similar to chromatographic column supports is common in other applications as well. For example, the use as catalysts of aerogels containing minor impurities is well known. Such catalysts have been used, for example, in the conversion by nitric oxide of paraffins, olefins, and alkylaromatics into nitriles. Such catalysts are typically activated by exposing the catalyst to oxygen or an oxygen-containing gas at extremely elevated temperatures, such as, for example, 400° C. and above for 24–48 hours, or about the time required for spinel formation. Such catalysts have been investigated in, for example, Rahman et al, *Applied Catalysis*, Vol. 36, pp. 209–220 (1988). However, exposure of the aerogel catalysts to high temperature during activation can have an undesired effect on other properties of the catalyst, such as the textural and structural aspects thereof, and has given rise to attempts to avoid high temperature activation. From U.S. Pat. No. 3,963,646 to Teichner et al., for example, it is known to form hydrogenation or controlled oxidation catalysts by coprecipitation of mixtures of hydrolyzable salts of a transition metal and a refractory metal oxide in a non-aqueous solvent with the simultaneous addition of a stoichiometric amount of water, followed by drying of the coprecipitate under hypercritical conditions.

Membranes have a significant role in industrial processing, especially in the biotechnology, gas separation and drug delivery device areas. The preparation of membranes having assymmetrical physical and surface-chemical properties has been described, for example, in Haggin, *Chemical and Engineering News*, p. 25–32 (Jul. 11, 1988). Such membranes have been used in membrane reactors which combine catalytic reaction with product separation. Successful membrane reactors require surface chemistry which varies with location in the cross-section of the membrane. However, the layering of different materials to form such composite membranes involves a difficult fabrication and results in the deposition of inherently thick layers.

Various techniques are known for the plasma activated chemical vapor deposition onto a substrate. For example, from U.S. Pat. No. 3,826,226 to Clark, it is known to deposit a controlled thickness metallic coating such as gold, silver, copper or aluminum onto small particles such as glass spheres using a drop tower for gravity feed of the particles through a vapor coating chamber. An ion beam which is disposed laterally offset from and optically shielded with respect to the drop tower provides a vaporized coating medium in the coating chamber.

From U.S. Pat. No. 4,268,711 to Gurev, it is known to deposit a thin film onto a substrate from a vapor employing a contained plasma source wherein a chemical reaction, such as between aluminum trichloride, silane and oxygen to produce vapors of silicon dioxide and aluminum oxide, takes place within the plasma and/or at the substrate surface being coated which is maintained at a low temperature.

From U.S. Pat. No. 4,583,492 to Cowher et al., it is known to use a plasma-enhanced vapor deposition reactor to coat a substrate with amorphous silica wherein the reactor is configured so as to avoid plugging of the vacuum pump associated with the reactor. Similar equipment and techniques are described, for example, in U.S. Pat. Nos. 4,608,063 to Kurokawa and 4,686,113 to Delfino et al.

In U.S. Pat. No. 4,362,632 to Jacob there is described a gas discharge apparatus wherein a perforated metallic cylinder is disposed concentrically within a reaction chamber so that activated gas introduced thereto provides very uniform distribution of gaseous excited species throughout the entire material processing volume within the cylinder to obtain very uniform chemical conversions therein.

U.S. Pat. No. 3,702,973 to Daugherty et al. teaches an apparatus for making ozone or other excited species which uses a laser to excite a gas flow, such as nitrogen, carbon dioxide or helium. In this apparatus, consideration is given to maintaining the plasma contained inside the electric discharge tube in a radially smooth condition by making the time required for diffusion to the surrounding wails equal to the ionization time.

U.S. Pat. No. 3,904,366 to Grasenick teaches an apparatus in which a sample material is exposed to an excited gas such as oxygen to convert the components of the substance into gaseous compounds which may be measured quantitively by an analytical method.

U.S. Pat. No. 4,756,794 to Yoder teaches an apparatus for etching the surface of a material such as diamond to remove a single atomic layer therefrom. In one embodiment described in this reference, energetic ions from an ion gun impinge on nitrogen oxide gas decomposing it into atomic oxygen and nitrogen so as to erode the surface.

A diffusion method of investigating surface recombination of hydrogen atoms and OH radicals using a sidearm reaction apparatus is described in Smith, *Journal of Chemical Physics*, vol. 11, pp. 110–125 (1943).

STATEMENT OF THE INVENTION

The invention provides a method of preparing a porous inorganic material with layered surface treatments. The method includes the sequential treatment of a solid porous structure of the material which has an exterior and an interior, wherein the interior comprises an interstitial surface, with a first surface treating agent to obtain a substantially uniform treatment of the interstitial surface. The method also includes the step of subsequently exposing the exterior to an oxidizing gas. The oxidizing gas contains an oxidizing species such as atomic oxygen or hydroxyl radical. This exposure is at conditions and for a time effective to oxidize or remove the first treating agent from an outer portion of the interstitial surface which is adjacent to the exterior, leaving an inner portion of the interstitial surface intact so that it remains treated with the first surface treating agent. The structure is then treated with a second surface treating agent. This obtains a structure having an inner layer of interstitial surface which is treated with the first agent, and an outer layer of the interstitial surface adjacent to the exterior which is treated with the second agent. Additional sequential oxidation/surface treatment cycles may be repeated, with each successive oxidation proceeding to a lesser depth beneath the exterior of the structure, in order to obtain a multi-layered structure of various surface treating agents.

The present invention also provides a porous structure of layered interstitial surface treatment obtained, for example, by the foregoing method. The material, which may be particulated microporous silica, is in a structure having an exterior and an internal interstitial surface underneath the exterior. An inner layer of the interstitial surface disposed from the exterior is treated with a first surface treating agent. An outer layer extending from adjacent the exterior to adjacent an intermediate layer, or the inner layer, is treated with a surface treating agent. The surface treatment of each layer is different from the surface treatments of the adjacent layer. If desired, the structure may also contain one or a plurality of intermediate layers disposed between the inner and outer layers, each inner, outer and intermediate layer having a different surface treatment than each layer adjacent thereto.

The invention also provides an atomic oxygen reactor. The reactor has a gas chamber, a source of oxidizing gas, at least one sidearm conduit and sample positioning means. The gas chamber is provided for flowing gas therethrough in an axial direction thereof. The gas source contains oxidizing species selected from, for example, atomic oxygen and hydroxyl radicals, for introduction into the gas chamber. Each sidearm conduit is in fluid communication with the gas chamber and extends transversely therefrom. The positioning means is provided for positioning in the sidearm conduit a sample to be exposed to the oxidizing species. The sample is positioned transversely across an end of the sidearm conduit disposed from the chamber for substantially uniform reaction with the oxidizing species. The characteristic diffusional relaxation time of the sidearm conduit is substantially less than the time required for all oxidizing radicals in the sidearm conduit to recombine. The specific design of this sidearm atomic oxygen reactor eliminates any significant radial concentration gradients of atomic oxygen, hydroxyl radicals or other oxidizing species in the sidearm conduit, and provides a uniform atomic oxygen and/or hydroxyl radical dose delivered to the specimen surface. Thus, the specimen surface will be uniformly reacted with the atomic oxygen or other oxidizing species in the sidearm reactor.

The invention further provides a method of activating aerogel catalysts. The method includes the steps of exposing the aerogel catalyst to an oxidizing gas containing atomic oxygen or hydroxyl radicals at a low temperature below about 100° C., for example, and recovering aerogel catalyst activated by the exposure. The aerogel catalyst may comprise silica or alumina and minor amounts of transition metals such as, for example, nickel. Still further, the invention provides aerogel catalysts activated by atomic oxygen at a low temperature.

DETAILED DESCRIPTION OF THE PREFERRED EMBODIMENTS

A porous structure of layered interstitial surface treatments can be obtained by sequentially treating the structure with a surface treating agent, removing an outer layer of the surface treating agent using an oxidizing plasma and treating the structure with a second surface treating agent. Porous structures suitable in the present invention include any porous solid material which is essentially inert in an oxidizing plasma or atomic oxygen-containing atmosphere. Inorganic materials such as refractory metal oxides are well suited as the base structure in the present invention, preferably alumina, and especially silica. Microporous silica particulates or beads are generally composed of agglomerated silica microspheres and have effective pore diameters in the range of from about 1 to about 10,000 Å, preferably from 10 to 1000 Å and especially, for silica supports used in chromatography, from about 30 to about 500 Å. The porous structure may be in the form of a sphere or other particulate, tube, rod, sheet or membrane, or the like, depending upon the desired use for the multilayered structure. For convenience clarity and the purpose of illustration only, reference is made herein to microporous spherical silica particles with the understanding that other microporous structures may also be suitably employed in the present invention.

The preparation of the plural-layered porous structure involves the treatment of the interstitial surface of the internal pores or voids in the microporous structure. Any surface treating agent capable of bonding with the material of the structure is generally suitable. It will be readily appreciated that the surface treating agent will also be capable of diffusing into the interstices or pores of the structure, i.e. it should be smaller than the effective pore size. A surface treating agent, other than the final surface treating agent, is also desirably reactive with atomic oxygen and/or hydroxyl radicals so that it can be removed from the internal surfaces by reaction therewith. The surface treating agent may be hydrophilic, hydrophobic, amphiphilic, ionic, or capable of covalently adsorbing an isolate, as desired. The surface treating agent itself may have functional groups which are in turn reactive with additional modifying agents. Thus, the surface treatment step may include an intermediate step wherein a modifying agent is used to derivatize, or couple with, the surface treating agent by reaction with functional groups thereof. For silica structures, a suitable surface treating agent is a silylating agent, such as, for example, hexamethyldisilazane, dimethyldichlorosilane, octadecyl dimethylchlorosilane, and the like. Surface treating agents, such as silylating agents, are well known in the art and are used commercially to manufacture various silica separation media. Silica particles treated with various surface treating agents are also commercially available and widely used in the chromatographic separation arts.

Figure 1A:
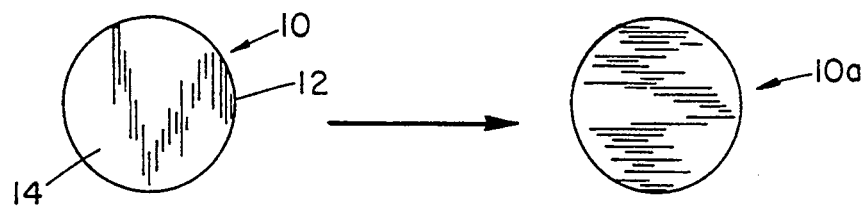
FIGS. 1A–C schematically represent the consecutive reaction of a porous solid spherical structure with a first surface treating agent (FIG. 1A), atomic oxygen (FIG. 1B) and a second surface treating agent (FIG. 1C), according to the present invention.
Figure 1B:
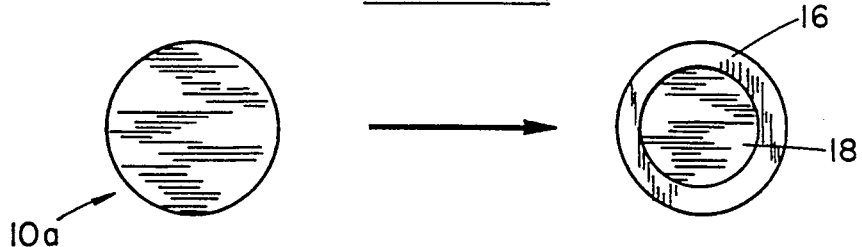
Figure 1C:
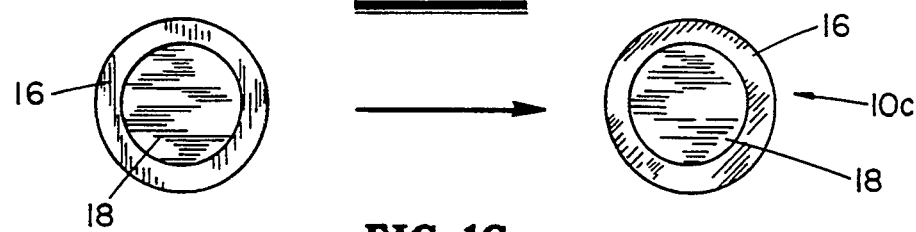

The method of the invention is described in reference to FIGS. 1A, 1B and 1C. The initial surface treating step of a silica bead or spherical particle 10 is illustrated schematically in FIG. 1A. The silica particle 10 has an exterior 12 and internal interstitial surface 14. The surface 14 comprises the walls of the interstitial pores, voids, spaces or channels in the microporous particle 10. When the particle 10 is treated with the first surface treating agent, both the exterior 12 and the internal surface 14 are treated with the surface treating agent which bonds thereto. The uniformly surface-treated particle $10a$ is then subjected to oxidation with atomic oxygen and/or hydroxyl radicals as illustrated schematically in FIG. 1B. The oxidation serves to remove the surface treating agent from an outer layer 16 of the internal interstitial surface while leaving an inner region or layer 18 modified with the first treating agent. The depth of outer layer 16 is determined primarily by the amount of oxidizing agent with which the particle $10a$ is reacted, i.e. more atomic oxygen reaction with the particle results in a greater depth of the layer 16. Then, as depicted in FIG. 1C, a second treating agent is used to modify the outer layer 16, but the inner layer 18 is generally unaffected since its bonding sites are occupied or blocked by the first surface treatment. Thus, in the particle $10c$, the outer layer 16 is modified with a second surface treating agent and the inner layer 18 remains modified with the first surface treating agent in a bilayer configuration.

If desired, the foregoing alternating surface treatments and oxidations may be repeated a plurality of times, with each subsequent oxidation proceeding to a lesser depth than the preceeding oxidation step, and with each successive surface treating agent being different than the surface treating agent in the immediately preceeding step. The particle thus produced has a multilayered interstitial internal surface wherein the depth of each layer is controlled by the subsequent amount of oxidation effected in the oxidizing plasma.

As mentioned above, each surface treatment step may include a derivitization step. Thus, for example, a derivitizable treating agent may be employed in a surface treatment step. Then following the subsequent oxidation thereof to strip away an outer layer of the derivitizable treating agent treatment, the remaining layer is derivitized to yield the desired surface treatment. This has the advantage of conserving the derivitizing agent which can in some instances be quite valuable, and also conserving atomic oxygen where the initial derivitizable surface treating has a lower molecular weight than the corresponding derivitized surface treatment. As one example, the initial surface treating agent may comprise an aminoalkyl silylating agent, and the derivitizing agent may comprise a peptide having blocked functionalities except for a C-terminus carboxyl group which has been converted to a corresponding acid arthydride, acid halide (e.g. chloride), carbonyldiimidazole, or a similar functional group capable of binding the peptide to the primary amine of the aminoalkyl bonded silica surface. In this embodiment, the remaining untreated outer layer may be subsequently treated with a surface treating agent which can be the same as or different than the preceeding derivitizable aminoalkyl silylating agent, and if desired, similarly derivitized.

The oxidation of the outer layer of porous internal surface area may be effected using conventional atomic oxygen reactors, including commercially available plasma ashers, or other suitable sources of atomic oxygen, such as, for example, ram flux in low earth orbit, laser photodissociation of parent molecules, and the like. Oxidation of the surface-treated microporous structure with highly reactive atomic oxygen has the advantage of obtaining a distinct oxidation reaction front, generally on the order of one effective pore diameter of the structure, a result not possible with less reactive molecular oxygen which does not obtain a sharp reaction front. In addition, atomic oxygen does not require the high temperatures that thermal, molecular oxygen requires, so there are no thermally induced changes in the physical or structural characteristics of the microporous structure when the atomic oxygen is used at a low temperature, preferably below about 100° C., and more preferably below about 40° C.

Figure 2:
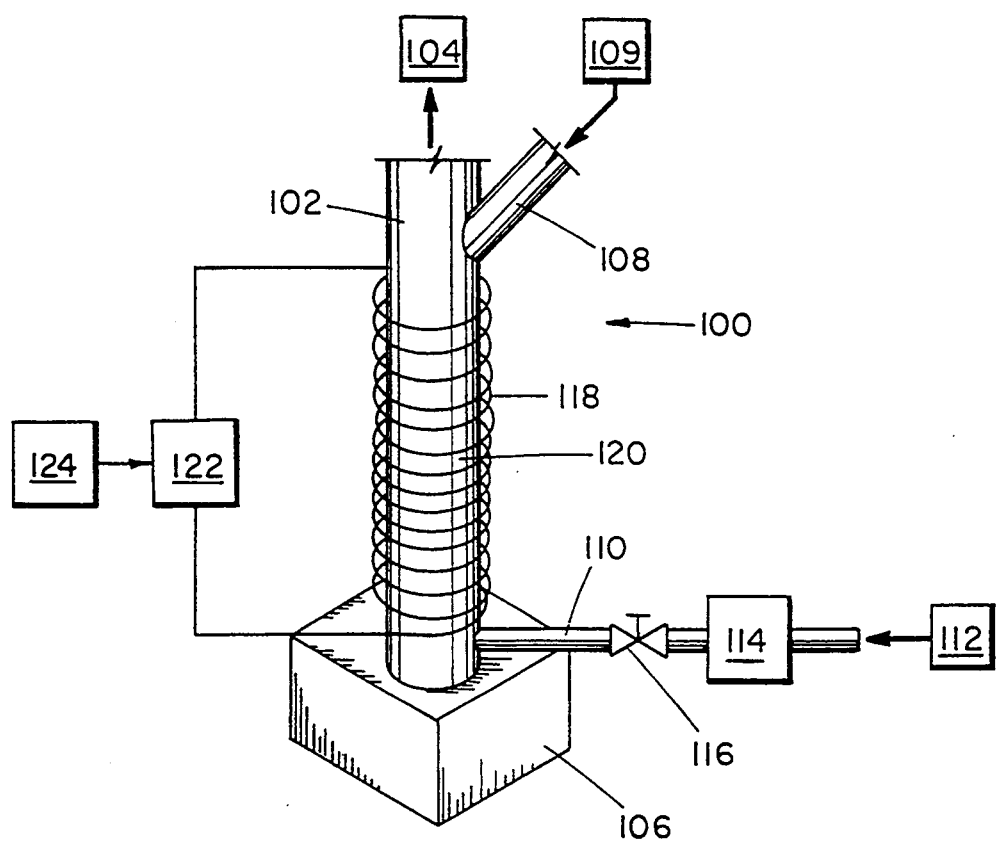
FIG. 2 is a schematic representation of a drop tower designed for the oxidation of porous solids wherein the porous solid descends through an atomic oxygen treatment section, according to the present invention.

In one preferred embodiment a drop tower is used to effect plasma oxidation of silica particles to the desired depth. In FIG. 2 there is shown a drop tower 100 having a vertical section 102 connected to a vacuum pump 104 at the top thereof and a product receiver 106 at the bottom thereof. A chute 108 is provided adjacent the top of the vertical section 102 for the introduction of the silica or aerogel particles, or other porous solid material to be treated in the oxidizing plasma, from silica particle source 109. A gas inlet 110 is provided in the lower portion of the vertical section 102 adjacent the product receiver 106, for introducing a gas from gas supply 112 via flow controller 114 and metering valve 116. An inductive coil 118 is provided around the vertical section 102 in an atomic oxygen treatment section 120. The coil 118 is part of a circuit including a matching network 122 and an RF generator 124 for producing an RF field in the treatment portion section 120 to generate oxidizing species in the gas.

In the operation of the drop tower 100 oxidizing gas from the gas supply 112 is metered at the desired rate into the vertical section 102 via the gas inlet 110. The gas flows upwardly through the vertical section 102 including the treatment portion 120 and exits the top of the vertical section 102 to the vacuum pump 104. The vacuum pump 104 is operated to maintain the desired vacuum in the vertical section 102, typically on the order from about 10 to about 150 Pa. The inductive coil 118 is used to couple an electromagnetic field of the gas in the treatment section 120 by operating the RF generator 124 with the impedance matching network 122 at the desired frequency and power consumption levels, typically about 13.5 MHz and up to several hundred watts of power, in a manner well known in the art.

Silica particles are introduced through the chute 108 to fall through the treatment section 120 into the product receiver 106 wherein they are collected. The upward velocity of the gas in the vertical section 102 must, of course, be less than the terminal velocity of the silica particles so that the silica particles will fall through the treatment section 120 rather than be carried overhead with the gas into the vacuum pump 104. Conventional protection devices may be employed in association with the vacuum pump 104 to protect the vacuum pump 104 from any accidental release of particles from the vertical section 102. If desired, the particle source 109 may comprise various conventional equipment employed to introduce the silica particles into the chute 108, such as, for example, a feed hopper, feed hopper agitator, feed valve, means for imparting a spinning motion to the silica particles (such as a rotating drum with knurling grooves as described in U.S. Pat. No. 3,826,226), and the like. The process is run until the desired quantity of product has accumulated in product receiver 106, or may be continuous where provision is made for removal of the accumulated products.

The depth of the outer layer of the silica particle from which the previous surface treating agent is removed in the drop tower 100 is controlled primarily by the concentration of atomic oxygen in the treatment section 120, as well as the residence time of the silica particle in the treatment section 120.

Figure 3:
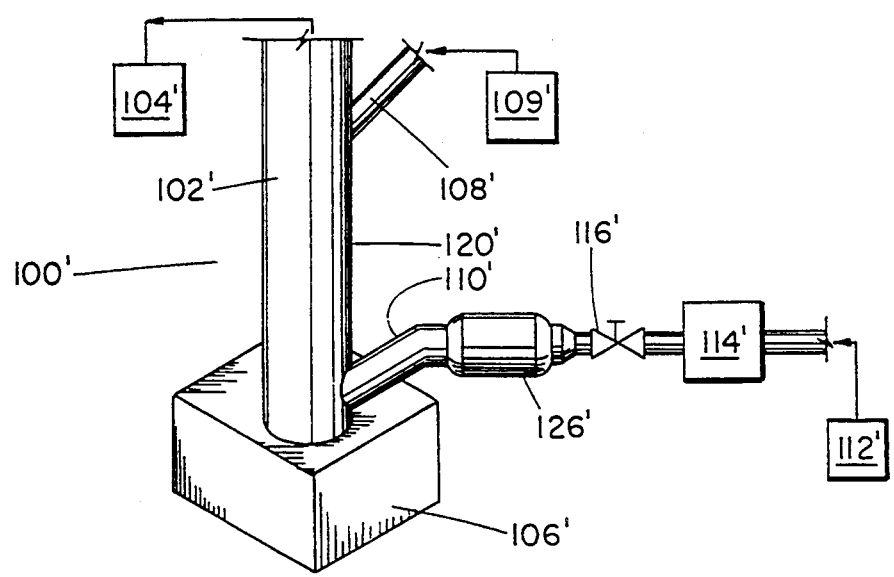
FIG. 3 is an alternative embodiment of the drop tower of FIG. 2 wherein atomic oxygen is provided as an afterglow from a microwave discharge cell or other source of atomic oxygen-containing gas.

The drop tower 100' illustrated in FIG. 3 is an alternate embodiment to that illustrated in FIG. 2. The parts of the drop tower 100' in FIG. 3 are similar to those parts bearing similar reference numerals in the drop tower 100 illustrated in FIG. 2. However, the inductive coil 118, network 122 and RF generator 124 are replaced with a microwave discharge cell 126', or other means for inducing atomic oxygen formation, positioned along the gas inlet line 110'. The microwave discharge cell 126' may comprise, for example, a microwave power supply with an Evanson-type discharge cavity to generate a discharge in gas flowing therethrough. This produces an afterglow environment in the treatment section 120' from which is eliminated the thermal effects, and charged particle and UV bombardment effects, typically associated with plasma asher environments, such as that existing in the treatment section 120 of the drop tower 100 of FIG. 2, unless a Faraday cage is used. On the other hand, atomic oxygen concentrations are typically lower in an afterglow environment than they are in a plasma asher environment so that longer residence times, and consequently a comparatively longer treatment section 120' may be required in the drop tower 100' of FIG. 3.

Figure 4:
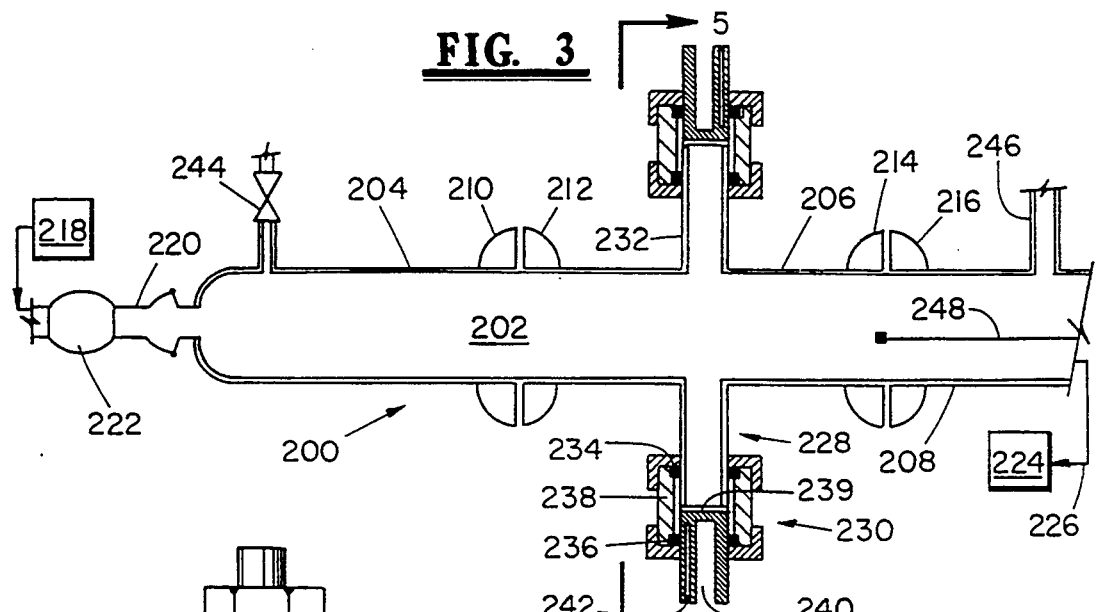
FIG. 4 is a schematic cross-sectional view of a sidearm atomic oxygen reactor according to the present invention.
Figure 5:
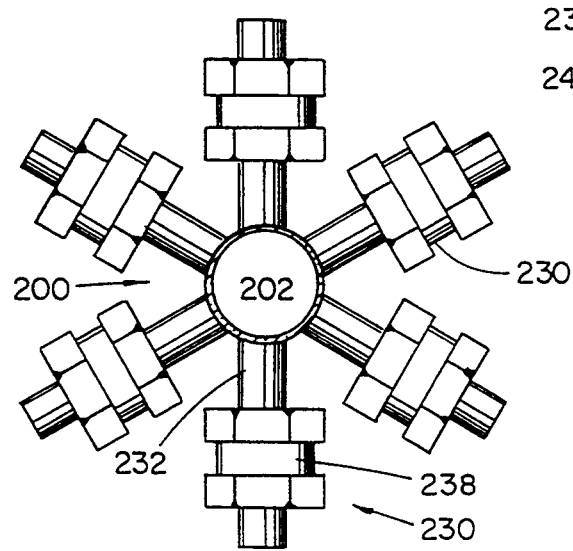
FIG. 5 is a cross-sectional view of the sidearm atomic oxygen reactor of FIG. 4 as seen along the lines 5—5.

When uniform treatment of a flat surface or thin porous membrane is desired, a sidearm atomic oxygen reactor 200 which is best seen in FIGS. 4 and 5 is preferred for the oxidation step. The device 200 is more practical when it is desired to uniformly treat structures having relatively large flat surfaces which are not practically treated using the drop tower devices of FIGS. 2 and 3, but where it is still necessary to obtain a uniform depth of reaction with atomic oxygen across the specimen surface. The sidearm atomic oxygen reactor 200 has a longitudinally oriented flow chamber 202 which may be appropriately constructed of glass or another suitable material in sections, e.g. inlet section 204, mid section 206 and discharge section 208, which are conveniently secured together using conventional coupling flanges 210, 212, 214 and 216. A gas flow source 218 supplies gas through inlet line 220 into the inlet section 204 of the chamber 202. A discharge generating apparatus 222 is positioned in the line 220 to generate a discharge in the gas flowing therethrough. A microwave power supply operating at 2450 MHz, such as that obtained under the trade designation Raytheon PGM-10, used with an Evanson-type discharge cavity, has been found to be suitable for this purpose. The gas entering the chamber 202 in the inlet section 204 flows axially therethrough and is discharged from discharge end 208 to a vacuum pump 224 via line 226 in fluid communication therebetween. A plurality of sidearms 228 are positioned on the mid section 206 transversely to the longitudinal axis thereof. The sidearms 228 are preferably radially symmetrical and six sidearms 228 are illustrated here for the purposes of an example, but any number more or less than six may be suitably used. A specimen holder 230 is positioned at a distal end of each sidearm conduit 232. The specimen holder 230 may be made, for example, by modifying a conventional union fitting, such as a Cajon brand union, drilled through to remove internal lips and to include the 0-ring vacuum seals 234, 236 at either end of a sleeve member 238 adjacent the conduit 232, so that disk-shaped specimen 239 can be held therein. If desired, each specimen holder 230 may also include specimen heater well 240 and thermocouple well 242. Alternatively, the specimen holder 230 may be provided with an adjusting mechanism to vary the distance of the specimen from the sidearm entrance, for example, using an insert (not shown) slidably engaged in the conduit 232. The chamber 202 may further optionally include conventional sampling and probing means and apparatus, such as, for example, an $NO_2$ supply and metering valve connected at 244 onto inlet section 204 of the chamber 202, a capacitance manometer connection 246 on discharge section 208, catalytic atomic oxygen probe 248 positioned adjacent the sidearms 228, and the like.

The sidearms 228 are constructed and operated so that no significant radial concentration gradients exist and a uniform atomic oxygen dose is thereby delivered to the specimen surface 239 which is held or secured transversely in the specimen holder 230. The elimination of radial concentration gradients in the sidearms 228 is determined by the relative magnitude of two characteristic relaxation times, $T_{diff}$ and $T_{rcm}$ wherein $T_{diff}$ is the characteristic diffusional relaxation time for the sidearm 228 and $T_{rcm}$ is the time required for all atomic oxygen in the sidearm to recombine. When $T_{diff}$ is much less than $T_{rcm}$, then no significant radial concentration gradients exist and a uniform atomic oxygen dose is delivered to the specimen surface. $T_{diff}$ is determined according to the equation:

$$T_{diff} = R^2/D$$

wherein R is the diameter of the sidearm conduit and D is the atomic oxygen diffusion coefficient (about 120 cm$^2$/s in air at 65 Pa). $T_{rcm}$ is determined according to the equation:

$$T_{rcm} = R/r_c v$$

wherein $r_c$ is the fraction of oxygen atoms which recombine upon striking the sidearm surface (about $3.2 \times 10^{-4}$ in the case of glass) and v is the mean thermal speed of oxygen atoms (about $6.3 \times 10^4$ cm/s at 300° K.). Thus, when R=1 cm and the reactor is operated at 65 Pa and 300° K., $T_{diff}$ is about 0.008 seconds and $T_{rcm}$ is about 0.1 seconds. Thus, the side-arm reactor can be used to provide a predetermined, uniform dose rate of atomic oxygen across the specimen surface, avoiding complications resulting from the effects of boundary-layer mass transfer which are substantially absent in the present device.

As an example, an atomic oxygen concentration in the gas chamber at the entrance to the side arm conduit of about $1 \times 10^{16}$ atoms/cm$^3$, or about 5 percent of the flowing gas at 65 Pa, can be produced using conventional atomic oxygen production. Higher atomic oxygen concentration in the gas chamber would, of course, obtain higher atomic oxygen dose rates, whereas lower pressures, e.g. 13 Pa or lower, would tend to increase the atomic oxygen dose rate, as well as the diffusion constant (which would increase the value of $T_{diff}$).

The atomic oxygen dose rate can be estimated by analytical solution of the partial differential equation describing the diffusional transport and first order or pseudo-first order atomic oxygen reaction processes:

$$k_c C(r,z) = D \frac{1}{r} \frac{\partial}{\partial r} rC(r,z) + \frac{\partial^2}{\partial z^2} C(r,z)$$

wherein $k_c$ is the rate constant for atomic oxygen loss in the sidearm conduit from all first order processes, C is the atomic oxygen concentration, r is radial position from the longitudinal axis of the sidearm conduit, and z is an axial position (distance from the sidearm conduit entrance from the main gas chamber), with the boundary conditions:

$$C(r,z) = C_o, \text{ at } z=0; \text{ and}$$

$$-D \frac{\partial}{\partial z} C(r,z) = k_s C(r,z), \text{ at } z = z_1 \text{ (the specimen surface)};$$

wherein $k_s$ is the rate constant for atomic oxygen loss at the specimen surface. If $T_{diff} < < T_{rcm}$, the partial differential equation simplifies to:

$$\frac{k_c C(z)}{D} = \frac{\partial^2}{\partial z^2} C(z).$$

A general solution to this has the form:

$$C(z) = A \exp[-(k_c/D)^{0.5}z] + B \exp[(k_c/D)^{0.5}z]$$

wherein A and B are constants determined by application of the boundary conditions as follows:

$$A = \frac{G_B C_O}{G_A + G_B};$$

$$B = \frac{G_A C_O}{G_A + G_B};$$

wherein:
$$G_A = [D(k_c/D)^{0.5} - k_s] \exp[-k_c/D)^{0.5}z_1]; \text{ and}$$

$$G_B = [-D(k_c/D)^{0.5} + k_s] \exp[(k_c/D)^{0.5}z_1].$$

The complete analytical solution for the case of no radial concentration dependence and first order atomic oxygen loss processes is as follows:

$$C(z) = \frac{C_o}{(G_A + G_B)} \{[G_B \exp[-(k_c/D)^{0.5}z] + G_A \exp[(k_c/D)^{0.5}z]\}$$

The atomic oxygen dose rate can thus be estimated, and it is readily appreciated that the dose rate can be increased dramatically by increasing the atomic oxygen concentration at the sidearm conduit entrance (at z=0), and altered by the material of the sidearm conduit and the specimen material. Total atomic oxygen doses of about $10^{24} - 10^{26}$ cm$^{-2}$ day$^{-1}$ or more can be obtained with this apparatus.

The foregoing oxygen reactors, as well as other more conventional atomic oxygen sources, also find application in the activation of silica and alumina aerogel catalysts therewith. Such catalysts have heretofore been activated by thermal molecular oxygen at elevated temperatures for extended periods of time, e.g. 410° C. for 48 hours. According to the present invention such catalysts are activated by exposing them to atomic oxygen at a relatively low temperature, preferably below about 100° C. and more preferably below about 40° C., for a period of time effective to activate the aerogel for catalytic purposes, preferably for about 24–48 hours.

Aerogels suitably employed herein include nickel oxide on alumina aerogel catalysts described, for example, in Rahman et al., supra, which is hereby incorporated herein by reference. Briefly, the aerogel comprises a transition metal oxide dispersed or supported on a highly porous refractory oxide. Suitable transition metals are, for example, iron, cobalt and especially nickel. Suitable refractory oxides include silica, and especially alumina. The preparation and use of such supported catalysts is well known by the artisan. The present method for activating such catalysts with atomic oxygen, however, has the advantage that a novel low-temperature activated aerogel catalyst is obtained which is essentially free of the physical and textural changes occasioned by high temperature activation, and further, the activated catalyst is more specific toward certain reactions than the corresponding thermally activated aerogels when used in conventional catalytic processes.

The invention is illustrated by way of the examples which follow.

EXAMPLE 1

Cubes of waterproofed silica were exposed to atomic oxygen to demonstrate the stripping away of an outer layer of a porous structure. The cubes measured 2.54 cm on each side and were obtained from Lockheed Missile and Space Corporation as LI 900 space shuttle orbiter thermal protection the material believed to contain silica fibers suspended in silica gel material fired to remove water. The cubes were cut from the tile material with a band saw and water-proofed with dimethylethoxysilane. The cubes were placed in the bottom of a cylindrical treatment chamber of an LFE Corporation model LTA-302 low temperature plasma asher. The longitudinal axis of the treatment chamber was horizontal so that only opposite lower edges of the cubes were in contact with the chamber wall. The plasma asher was operated at 13.56 MHz using 100 watts of forward RF power with a working gas pressure of about 3500 Pa (267 Torr). The working gas was Liquid Air Corporation (analyzed >99.5% pure) aviator's breathing oxygen containing 12 ppm total hydrocarbon and less than 4 ppm water vapor. The cubes were subjected to treatment in the plasma asher for a period of time from about 2 minutes to about 2 hours. The cubes were removed from the asher and immersed in an aqueous solution containing methylene blue dye for a few minutes. The cubes were then cross-sectioned with a hack saw. The outer portion of the cubes which were treated in the plasma asher for a period of time of 30 minutes or less were seen to be blue and were easily wetted with water, but the inner portion was still white, fully hydrophobic and appeared cubical in shape. The size of the hydrophobic core region depended on the duration of exposure to the oxygen plasma, and the cubes absorbed the aqueous blue dye to a depth determined by the progress of the atomic oxygen reaction front. Cubes exposed to the oxygen plasma for a period of time greater than 30 minutes did not contain an inner hydrophobic core and absorbed blue dye to the center of the cube.

EXAMPLE 2

Chromatographic packing material was treated with a hydrophobic surface agent and exposed to oxygen plasma to demonstrate the partial removal of a hydrophobic surface treatment. Porous silica spheres having a size distribution between 80 and 100 mesh were obtained under the trade designation PORASIL. The spheres were treated with dimethylethoxysilane as described in Example 1. The resulting spheres were fully hydrophobic and floated on deionized water. The treated spheres were placed in the oxygen plasma asher described in Example 1 in a monolayer arrangement. Exposure of the silica spheres to oxygen plasma for 30 seconds produced silica spheres which still floated but were wet by the water, indicating that the outer region of the porous silica spheres had become hydrophilic while the inner region remained hydrophobic from the dimethylethoxysilane treatment. Prolonged treatment of the silica spheres in the oxygen plasma asher resulted in progressive loss of hydrophobic properties until the spheres behaved like the starting PORASIL material before treatment with dimethylethoxysilane.

EXAMPLE 3

Chromatographic separation of the octapeptide Angiotensin II from serum or plasma is effected with silica particles having an inner internal layer surface treated with phenyl groups, and an outer internal layer and exterior surface-treated with phosphorylcholine groups. Silica particles are treated with phenyl dimethylchlorosilane (product PO160 from Petrarch) to obtain uniform surface treatment of the particle surfaces with pendant phenyl groups. The particles are then briefly exposed to remove the phenyl groups from the particle exterior and in a layer of relatively small depth adjacent the exterior. The particles are then treated with dimethyldichlorsilane (product D5550 from Petrarch) and a phosphorylcholine (see Durrani, et al., "Modification of Polymer Surfaces for Biomedical Application," in chapter 10 of *Polymer Surface Interfaces*, Feast et al. (ed.), pp. 189–200 (Jon Wiley & Sons, Ltd. 1987) of the formula:

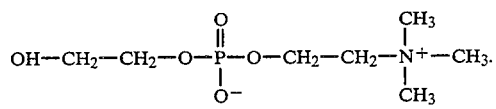

This is done according to well known techniques for treating silica particles therewith, except that the interior layer of phenyl-treated surface is "blocked" against the phosphorylcholine treatment. The resulting particles have an innermost layer with phenyl groups on its surface and an outer layer and exterior with pendant phosphoryl choline groups. In HPLC, the octapeptide is adsorbed and thereby separated by the interior phenyl groups, while the serum or plasma proteins are excluded by the phosphorylcholine-treated hydrophilic outer layer.

EXAMPLE 4

Chromatographic separation of natriuretic peptide (ANP) from whole serum, or of β-endorphins from tissue preparations, is effected with silica particles having an inner region of octadecyl surface treatment and an exterior region of phosphorylcholine treatment. The silica particles are treated as in Example 3, except that octadecyl-bonded porous silica (obtained commercially, e.g. from Analytchem International) is used instead of phenyl dimethylchlorosilane-treated silica. In HPLC, the ANP and/or β-endorphins are adsorbed and thereby separated by the interior octadecyl groups, while the serum and tissue proteins are excluded by the phosphorylcholine groups in the outer layer.

EXAMPLE 5

Chromatographic separation of catecholamines from plasma or urine is effected with silica particles having an interior layer surface treated to have pendant vicinal diol groups and an exterior layer surface treated to have pendant phosphorylcholine groups. Silica particles are treated with a phenylboronic acid silyating agent, e.g., of the formula:

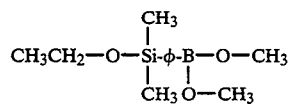

The particles are subsequently exposed to atomic oxygen for a brief period to burn off an outer layer of the surface treatment for a small depth, while generally retaining the phenylboronic acid treatment of the innermost layer, and the particles are washed in deionized water to remove residual boric acid product. The particles are then treated with dimethyldichlorosilane and the phosphorylating surface treating agent of Example 3 as described therein. In HPLC, the interior layer adsorbs catecholamines while the exterior layer excludes proteins in the plasma or urine.

EXAMPLE 6

Silica beads are surface treated with an aminobutyl silylating agent such as 4-aminobutyl dimethyl methoxysilane obtained as product AO695 from Petrarch. The surface aminobutyl groups are removed from an outer layer with atomic oxygen. The beads are then treated with a solution of a peptide having a C-terminal carboxyl group derivitized as an acid anhydride, acid chloride, carbonyldiimidazole or the like, and all other functionalities blocked with a conventional blocking agent. The peptide thus binds to the aminobutylated inner layer, but does not bind to the outer layer wherein the aminobutyl groups have been removed. The beads are then treated with aminobutyl silylating agent to aminobutylate the outer layer surface, but the inner layer is not aminobutylated because there are no silica groups available therefor. The beads are then treated with a solution of the carbonyldiimidazole derivative of a lecithin carboxylic acid having an acid functionality from 1,12-dodecanedicarboxylic acid as described in Pidgeon, *Chemical and Engineering News*, pp. 23–24 (Dec. 12, 1988). The resulting silica beads are useful for separating a peptide-specific isolate while the proteins in the sample are excluded by the hydrophilic outer layer.

EXAMPLE 7

Nickel oxide on alumina aerogel catalyst having a surface area of about 200 m$^2$/g obtained from R. J. Willey and prepared as described in Rahman et al., supra, was activated in the plasma asher as described in Example 1 using a pressure of 26 Pa. A sample of 100 mg was spread evenly over the bottom of a glass boat placed in the bottom of the plasma chamber. The sample was stirred once at 8 hours, and removed after 23 hours. The resulting catalyst was active and had better selectivity for acrylonitrile production in the nitroxidation of propylene than the same catalyst activated in air at 410° C. for 48 hours.

The invention is described hereinabove by way of illustration, and various modifications in the details thereof will become apparent to those skilled in the art in view thereof. All such variations within the scope and spirit of the appended claims are intended to be embraced thereby.

I claim:

1. An atomic oxygen reactor, comprising:
   a gas chamber for flowing gas therethrough in an axial direction;
   a source of gas containing atomic oxygen, connected to said chamber, for introduction of said gas into said chamber;
   at least one sidearm conduit in fluid communication with said gas chamber and extending transversely therefrom; and
   means for positioning a sample to be exposed to said atomic oxygen transversely across an end of said sidearm conduit disposed from said chamber for substantially uniform reaction therewith;
   wherein said at least one sidearm conduit is constructed and arranged such that a characteristic diffusional relaxation time of said at least one sidearm conduit is substantially less than the time required for all atomic oxygen in the sidearm conduit to recombine.

2. An atomic oxygen reactor, comprising:
   a gas chamber having an inlet and an outlet and comprising means for flowing gas therethrough in an axial direction;
   a source of gas, containing atomic oxygen, connected to the inlet of said chamber for introduction of said gas into said chamber;
   at least one sidearm conduit in fluid communication with said gas chamber between said inlet and said outlet and extending transversely relative to the axis upon which gas is caused to flow through said gas chamber; and
   means for positioning a sample to be exposed to said atomic oxygen within said at least one sidearm conduit in a portion of said sidearm conduit spaced from said chamber for substantially uniform reaction with said atomic oxygen;
   wherein said at least one sidearm conduit is constructed and arranged such that a characteristic diffusional relaxation time of said at least one sidearm conduit is substantially less than the time required for all atomic oxygen in the sidearm conduit to recombine.

3. The apparatus of claim 2, wherein said sample to be exposed to said atomic oxygen extends transversely across said portion of said sidearm conduit spaced from said chamber.

4. The apparatus of claim 2, wherein said at least one sidearm conduit comprises a plurality of sidearm conduits extending from said gas chamber and mutually and angularly spaced around said gas chamber.

5. The apparatus of claim 4, wherein said sidearm conduits extend outwardly from said gas chamber along respective radial axes relative to the axis upon which said gas is caused to flow through said gas chamber.

* * * * *